US010065047B2

(12) United States Patent
Borsody

(10) Patent No.: US 10,065,047 B2
(45) Date of Patent: Sep. 4, 2018

(54) COORDINATING EMERGENCY TREATMENT OF CARDIAC DYSFUNCTION AND NON-CARDIAC NEURAL DYSFUNCTION

(71) Applicant: Nervive, Inc., Orinda, CA (US)

(72) Inventor: Mark Klingler Borsody, Orinda, CA (US)

(73) Assignee: Nervive, Inc., Orinda, CA (US)

( * ) Notice: Subject to any disclaimer, the term of this patent is extended or adjusted under 35 U.S.C. 154(b) by 672 days.

(21) Appl. No.: 14/282,997

(22) Filed: May 20, 2014

(65) Prior Publication Data

US 2014/0343349 A1    Nov. 20, 2014

Related U.S. Application Data

(60) Provisional application No. 61/855,599, filed on May 20, 2013.

(51) Int. Cl.
*A61N 2/00* (2006.01)
*A61N 1/365* (2006.01)
(Continued)

(52) U.S. Cl.
CPC ......... *A61N 2/002* (2013.01); *A61N 1/36014* (2013.01); *A61N 1/3625* (2013.01);
(Continued)

(58) Field of Classification Search
CPC .. A61N 2/002; A61N 1/3625; A61N 1/36014; A61N 2/006; A61N 1/365585;
(Continued)

(56) References Cited

U.S. PATENT DOCUMENTS 2,876,767 A    3/1959  Wasserman
3,629,521 A   12/1971  Puharich et al.
(Continued)

FOREIGN PATENT DOCUMENTS

CA    1 135 348 A    11/1982
CA    2 021 506 A1    2/1991
(Continued)

OTHER PUBLICATIONS

Australian Government, IP Australia, Patent Examination Report No. 1, Australian Patent Application No. 2011248487, Feb. 17, 2015, three pages.
(Continued)

*Primary Examiner* — Mark W Bockelman
(74) *Attorney, Agent, or Firm* — Fenwick & West LLP

(57) ABSTRACT

Herein is described a device and methods-of-use to treat multiple possible causes of sudden neurological dysfunction related to cardiac, cerebrovascular, or brain electrical abnormalities. The device can be employed so as to treat cardiac dysfunction such as arrhythmia and subsequently related dysfunction of the central nervous system such as stroke and seizure. Alternatively, the device can be employed so as to treat cardiac dysfunction simultaneous with treatment of dysfunction of the central nervous system. Finally, the device can be employed so as to augment the effectiveness of treating cardiac dysfunction, namely the restoration of cardiac output and blood flow to the brain, by dilating the arteries of the brain.

9 Claims, 5 Drawing Sheets

(51) Int. Cl.
*A61N 1/36* (2006.01)
*A61N 1/362* (2006.01)
*A61N 1/04* (2006.01)

(52) U.S. Cl.
CPC .............. *A61N 2/006* (2013.01); *A61N 1/046* (2013.01); *A61N 1/36017* (2013.01); *A61N 1/36025* (2013.01); *A61N 1/36585* (2013.01)

(58) Field of Classification Search
CPC . A61N 1/36017; A61N 1/046; A61N 1/36025
See application file for complete search history.

(56) References Cited

U.S. PATENT DOCUMENTS

| | | | |
|---|---|---|---|
| 4,044,774 A | 8/1977 | Corbin et al. |
| 4,696,287 A | 9/1987 | Hortmann et al. |
| 5,116,304 A | 5/1992 | Cadwell |
| 5,441,495 A | 8/1995 | Liboff et al. |
| 5,461,215 A | 10/1995 | Haldeman |
| 5,607,461 A | 3/1997 | Lathrop |
| 5,922,016 A | 7/1999 | Wagner |
| 5,991,664 A | 11/1999 | Seligman |
| 6,078,838 A | 6/2000 | Rubinstein |
| 6,093,417 A | 7/2000 | Petrus |
| 6,179,770 B1 | 1/2001 | Mould |
| 6,179,771 B1 | 1/2001 | Mueller |
| 6,179,772 B1 | 1/2001 | Blackwell |
| 6,213,933 B1 | 4/2001 | Lin |
| 6,310,961 B1 | 10/2001 | Oliveira et al. |
| 6,408,855 B1 | 6/2002 | Berrang et al. |
| 6,425,852 B1 | 7/2002 | Epstein et al. |
| 6,468,199 B1 | 10/2002 | Satou et al. |
| 6,488,617 B1 | 12/2002 | Katz |
| 6,526,318 B1 | 2/2003 | Ansarinia |
| 6,551,233 B2 | 4/2003 | Perreault et al. |
| 6,629,399 B2 | 10/2003 | Sarles et al. |
| 6,663,556 B2 | 12/2003 | Barker |
| 6,849,040 B2 | 2/2005 | Ruohonen et al. |
| 6,853,858 B2 | 2/2005 | Shalev |
| 6,900,420 B2 | 5/2005 | Markegård et al. |
| 6,926,660 B2 | 8/2005 | Miller |
| 7,103,417 B1 | 9/2006 | Segel et al. |
| 7,117,033 B2 | 10/2006 | Shalev et al. |
| 7,120,489 B2 | 10/2006 | Shalev et al. |
| 7,146,209 B2 | 12/2006 | Gross et al. |
| 7,146,227 B2 | 12/2006 | Dadd et al. |
| 7,149,574 B2 | 12/2006 | Yun et al. |
| 7,340,298 B1 | 3/2008 | Barbut |
| 7,363,076 B2 | 4/2008 | Yun et al. |
| 7,367,936 B2 | 5/2008 | Myers et al. |
| 7,396,326 B2 | 7/2008 | Ghiron et al. |
| 7,407,478 B2 | 8/2008 | Zangen et al. |
| 7,519,435 B2 | 4/2009 | Parker et al. |
| 7,561,919 B2 | 7/2009 | Shalev et al. |
| 7,580,754 B2 | 8/2009 | Zhang et al. |
| 7,591,776 B2 | 9/2009 | Phillips et al. |
| 7,591,779 B2 | 9/2009 | Kalinowski et al. |
| 7,601,115 B2 | 10/2009 | Riehl |
| 7,636,597 B2 | 12/2009 | Gross et al. |
| 7,640,062 B2 | 12/2009 | Shalev |
| 7,658,704 B2 | 2/2010 | Fox et al. |
| 7,684,858 B2 | 3/2010 | He et al. |
| 7,684,859 B2 | 3/2010 | Shalev et al. |
| 7,711,432 B2 | 5/2010 | Thimineur et al. |
| 7,771,341 B2 | 8/2010 | Rogers |
| 7,854,232 B2 | 12/2010 | Aho et al. |
| 7,946,973 B2 | 5/2011 | Peterchev |
| 7,973,635 B2 | 7/2011 | Baarman et al. |
| 7,976,451 B2 | 7/2011 | Zangen et al. |
| 7,998,053 B2 | 8/2011 | Aho |
| 8,052,591 B2 | 11/2011 | Mishelevich et al. |
| 8,267,850 B2 | 9/2012 | Schneider et al. |
| 8,277,371 B2 | 10/2012 | Zangen et al. |
| 8,388,510 B2 | 3/2013 | Zangen et al. |
| 8,396,566 B2 | 3/2013 | Kassab et al. |
| 8,412,342 B2 | 4/2013 | Zhang et al. |
| 8,460,167 B2 | 6/2013 | Chornenky et al. |
| 8,523,753 B2 | 9/2013 | Schneider et al. |
| 8,545,378 B2 | 10/2013 | Peterchev |
| 8,591,392 B2 | 11/2013 | Bentwich et al. |
| 8,723,628 B2 | 5/2014 | Mishelevich et al. |
| 8,771,163 B2 | 7/2014 | Zangen et al. |
| 8,795,148 B2 | 8/2014 | Schneider et al. |
| 2001/0031906 A1 | 10/2001 | Ishikawa et al. |
| 2002/0026125 A1 | 2/2002 | Leysieffer |
| 2002/0151886 A1 | 10/2002 | Wood |
| 2003/0004393 A1 | 1/2003 | Ewing et al. |
| 2003/0195588 A1 | 10/2003 | Fischell et al. |
| 2004/0220644 A1* | 11/2004 | Shalev ............... A61N 1/0546 607/45 |
| 2005/0027251 A1 | 2/2005 | Masters |
| 2005/0222486 A1 | 10/2005 | Shin et al. |
| 2005/0288664 A1 | 12/2005 | Ford et al. |
| 2006/0122675 A1 | 6/2006 | Libbus et al. |
| 2006/0162952 A1 | 7/2006 | Olbrich et al. |
| 2006/0187607 A1 | 8/2006 | Mo |
| 2006/0287566 A1 | 12/2006 | Zangen et al. |
| 2006/0287689 A1 | 12/2006 | Debruyne et al. |
| 2007/0118197 A1 | 5/2007 | Loeb |
| 2008/0027513 A1 | 1/2008 | Carbunaru |
| 2008/0058581 A1 | 3/2008 | Aho |
| 2008/0082141 A1 | 4/2008 | Risi |
| 2008/0097549 A1 | 4/2008 | Colbaugh et al. |
| 2008/0154343 A1 | 6/2008 | Li et al. |
| 2008/0224808 A1 | 9/2008 | Ghiron et al. |
| 2008/0262287 A1 | 10/2008 | Dussau |
| 2008/0262468 A1 | 10/2008 | Clifford et al. |
| 2009/0018384 A1 | 1/2009 | Boyden et al. |
| 2009/0099405 A1 | 4/2009 | Schneider et al. |
| 2009/0108969 A1 | 4/2009 | Sims et al. |
| 2009/0131739 A1 | 5/2009 | Shalev |
| 2009/0174407 A1 | 7/2009 | Han et al. |
| 2009/0187098 A1 | 7/2009 | Makower et al. |
| 2010/0003656 A1 | 1/2010 | Kilgard et al. |
| 2010/0016650 A1 | 1/2010 | Phillips et al. |
| 2010/0094076 A1 | 4/2010 | Phillips |
| 2010/0113959 A1 | 5/2010 | Pascual-Leone et al. |
| 2010/0114184 A1 | 5/2010 | Degtyar et al. |
| 2010/0193506 A1 | 8/2010 | Nagai et al. |
| 2010/0286470 A1 | 11/2010 | Schneider et al. |
| 2010/0331602 A1 | 12/2010 | Mishelevich et al. |
| 2011/0082326 A1 | 4/2011 | Mishelevich et al. |
| 2011/0125203 A1 | 5/2011 | Simon et al. |
| 2011/0218381 A1 | 9/2011 | Ruohonen |
| 2011/0263925 A1 | 10/2011 | Bratton |
| 2011/0306846 A1* | 12/2011 | Osorio ............... A61B 5/4094 600/301 |
| 2012/0101366 A1 | 4/2012 | Ruohonen et al. |
| 2012/0149969 A1 | 6/2012 | Farone |
| 2013/0096363 A1 | 4/2013 | Schneider et al. |
| 2013/0267763 A1 | 10/2013 | Schneider et al. |
| 2013/0278369 A1 | 10/2013 | Shepard et al. |
| 2013/0282071 A1* | 10/2013 | Matos ............... A61N 1/37282 607/4 |
| 2013/0304159 A1 | 11/2013 | Simon et al. |
| 2013/0317281 A1 | 11/2013 | Schneider et al. |
| 2014/0081072 A1 | 3/2014 | Huang et al. |
| 2014/0085031 A1 | 3/2014 | Nomura et al. |
| 2014/0163305 A1 | 6/2014 | Watterson |

FOREIGN PATENT DOCUMENTS

| | | |
|---|---|---|
| CA | 2 608 084 A1 | 11/2006 |
| CA | 2 610 991 A1 | 12/2006 |
| CN | 86105171 A | 3/1987 |
| CN | 101366666 A | 2/2009 |
| CN | 101985058 A | 3/2011 |
| CN | 102013579 A | 4/2011 |
| CN | 202605538 U | 12/2012 |
| CN | 202637725 U | 1/2013 |
| CN | 202961526 U | 6/2013 |
| DE | 10046275 A1 | 3/2002 |
| EP | 0 214 527 A1 | 3/1987 |

(56) References Cited

FOREIGN PATENT DOCUMENTS

| | | |
|---|---|---|
| EP | 0 408 230 A2 | 1/1991 |
| EP | 1 145 738 B1 | 10/2001 |
| EP | 1 671 672 A1 | 6/2006 |
| EP | 1 890 762 A2 | 2/2008 |
| EP | 1 890 615 A4 | 9/2009 |
| EP | 2 384 223 A2 | 11/2011 |
| EP | 2 520 334 A1 | 11/2012 |
| EP | 2 666 515 A1 | 11/2013 |
| JP | S62-44250 A | 2/1987 |
| JP | 2003-503119 A | 1/2003 |
| JP | 2003-180847 A | 7/2003 |
| JP | 2006-515999 A | 6/2006 |
| JP | 2008-522725 A | 7/2008 |
| JP | 2008-528145 A | 7/2008 |
| JP | 2010-213979 A | 9/2010 |
| RU | 2012 115 948 A | 10/2013 |
| WO | WO 1995/25417 A1 | 9/1995 |
| WO | WO 1997/00639 A2 | 1/1997 |
| WO | WO 2001/00273 A1 | 1/2001 |
| WO | WO 2001/97095 A2 | 12/2001 |
| WO | WO 2001/97905 A1 | 12/2001 |
| WO | WO 2002/32504 A2 | 4/2002 |
| WO | WO 2002/089902 A2 | 11/2002 |
| WO | WO 2003/026478 A2 | 4/2003 |
| WO | WO 2003/090863 A1 | 11/2003 |
| WO | WO 2004/036603 A1 | 4/2004 |
| WO | WO 2004/043217 A2 | 5/2004 |
| WO | WO 2004/043218 A2 | 5/2004 |
| WO | WO 2004/043334 A2 | 5/2004 |
| WO | WO 2004/045242 A2 | 5/2004 |
| WO | WO 2004/087255 A1 | 10/2004 |
| WO | WO 2005/002346 A2 | 1/2005 |
| WO | WO 2005/030025 A2 | 4/2005 |
| WO | WO 2006/014896 A1 | 2/2006 |
| WO | WO 2006/021957 A2 | 3/2006 |
| WO | WO 2006/040690 A2 | 4/2006 |
| WO | WO 2006/057734 A2 | 6/2006 |
| WO | WO 2006/076708 A2 | 7/2006 |
| WO | WO 2006/078924 A2 | 7/2006 |
| WO | WO 2006/083675 A2 | 8/2006 |
| WO | WO 2006/119512 A2 | 11/2006 |
| WO | WO 2006/134598 A3 | 12/2006 |
| WO | WO 2006/135853 A2 | 12/2006 |
| WO | WO 2007/137335 A1 | 12/2007 |
| WO | WO 2008/030485 A2 | 3/2008 |
| WO | WO 2008/048471 A2 | 4/2008 |
| WO | WO 2008/052166 A2 | 5/2008 |
| WO | WO 2008/112915 A1 | 9/2008 |
| WO | WO 2008/130533 A2 | 10/2008 |
| WO | WO 2008/150963 A1 | 12/2008 |
| WO | WO 2009/011939 A1 | 1/2009 |
| WO | WO 2009/013881 A1 | 1/2009 |
| WO | WO 2009/033144 A2 | 3/2009 |
| WO | WO 2009/033150 A1 | 3/2009 |
| WO | WO 2009/033192 A1 | 3/2009 |
| WO | WO 2009/037689 A2 | 3/2009 |
| WO | WO 2009/042863 A1 | 4/2009 |
| WO | WO 2009/047370 A2 | 4/2009 |
| WO | WO 2009/100633 A1 | 8/2009 |
| WO | WO 2009/138428 A2 | 11/2009 |
| WO | WO 2009/143171 A2 | 11/2009 |
| WO | WO 2010/014894 A1 | 2/2010 |
| WO | WO 2010/033909 A2 | 3/2010 |
| WO | WO 2010/049576 A1 | 5/2010 |
| WO | WO 2010/062622 A2 | 6/2010 |
| WO | WO 2010/080879 A2 | 7/2010 |
| WO | WO 2011/060699 A1 | 5/2011 |
| WO | WO 2012/045079 A9 | 4/2012 |
| WO | WO 2012/048319 A2 | 4/2012 |
| WO | WO 2012/090068 A2 | 7/2012 |
| WO | WO 2012/117166 A1 | 9/2012 |
| WO | WO 2013/006670 A2 | 1/2013 |
| WO | WO 2013/116235 A1 | 8/2013 |
| WO | WO 2013/126176 A1 | 8/2013 |
| WO | WO 2014/022236 A1 | 2/2014 |
| WO | WO 2014/097571 A1 | 6/2014 |

OTHER PUBLICATIONS

Bar-Shir, A. et al., "Late Stimulation of the Sphenopalatine-Ganglion in Ischemic Rats: Improvement in N-Acetyl-Aspartate Levels and Diffusion Weighted Imaging Characteristcs as Seen by MR," Journal of Magnetic Resonance Imaging, 2010, pp. 1355-1363, vol. 31.

Brainsgate, "Ischemic Stroke System," 2005, two pages. [Online] [Retrieved Oct. 19, 2011] Retrieved from the Internet <URL:http://www.brainsgate.com/eng/page.php?id=11&instance.sub.--id=8&-gt.

European Patent Office, Search Report and Opinion, European Patent Application No. 11778023.9, dated Jul. 31, 2014, eight pages.

European Patent Office, Search Report and Opinion, European Patent Application No. 12856454.9, dated Oct. 19, 2015, six pages.

Goadsby, P.J., "Characteristics of facial nerve-elicited cerebral vasodilatation determined using laser Doppler flowmetry," Database Accession No. NLM1992824, Jan. 1991, XP002711162, Database Medline, U.S. National Library of Medicine (NLM), Bethesda, Maryland, U.S.

Israel Patent Office, Office Action, Israeli Patent Application No. 222750, dated May 3, 2015, six pages.

Japanese Patent Office, Office Action, Japanese Patent Application No. 2013-509125, dated Oct. 1, 2014, eight pages.

Khurana, D. et al., "Implant for Augmentation of Cerebral Blood Flow Trial 1: A pilot Study Evaluating the Safety and Effectiveness of the Ischaemic Stroke System for Treatment of Acute Ischaemic Stroke," International Journal of Stroke, Dec. 2009, pp. 480-485, vol. 4.

PCT International Search Report and Written Opinion, PCT Application No. PCT/US2011/034378, dated Aug. 8, 2011, seven pages.

PCT International Search Report and Written Opinion, PCT Application No. PCT/US2012/067801, dated Apr. 19, 2013, twelve pages.

State Intellectual Property Office of the People's Republic of China, First Office Action, Chinese Patent Application No. 201180022239.3, dated Apr. 4, 2014, fifteen pages.

State Intellectual Property Office of the People's Republic of China, First Office Action, Chinese Patent Application No. 2012800598917, dated Mar. 19, 2015, sixteen pages.

Stjernschantz, J. et al., "Vasomotor effects of facial nerve stimulation: noncholinergic vasodilation in the eye," Acta Physiologica Scandinavica, May 1, 1980, pp. 45-50, vol. 109, No. 1, Scandinavian Physiological Society.

United States Office Action, U.S. Appl. No. 13/096,889, dated Jun. 18, 2014, twenty-five pages.

United States Office Action, U.S. Appl. No. 13/096,889, dated Jun. 26, 2015, thirteen pages.

United States Office Action, U.S. Appl. No. 13/096,889, dated Nov. 6, 2014, twenty-seven pages.

United States Office Action, U.S. Appl. No. 13/692,226, dated Jun. 10, 2014, nineteen pages.

United States Office Action, U.S. Appl. No. 13/692,226, dated Sep. 9, 2014, twenty-three pages.

United States Office Action, U.S. Appl. No. 15/056,326, dated Feb. 6, 2018, 13 pages.

Yarnitsky, D. et al., "Blood-brain Barrier Opened by Stimulation of the Parasympathetic Sphenopalatine Ganglion: A New Method for Macromolecule Deliver to the Brain," Journal of Neurosurgery, 2004, pp. 303-309, vol. 101.

Yarnitsky, D. et al., "Increased BBB Permeability by Parasympathetic Sphenopalatine Ganglion Stimulation in Dogs," Brain Research, 2004, five pages.

Yarnitsky, D. et al., "Reversal of Cerebral Vasospasm by Sphenopalatine Ganglion Stimulation in a Dog Model of

(56) References Cited

OTHER PUBLICATIONS

Subarachnoid Hemorrahage," Surgical Neurology, 2005, pp. 5-11, vol. 64.

* cited by examiner

COORDINATING EMERGENCY TREATMENT OF CARDIAC DYSFUNCTION AND NON-CARDIAC NEURAL DYSFUNCTION

RELATED APPLICATIONS

This application claims the benefit of U.S. Provisional Application No. 61/855,599 filed on May 20, 2013, entitled "Hybrid facial nerve stimulator—cardiac defibrillator," the entire disclosure of which is hereby incorporated by reference herein in its entirety for all purposes.

FIELD OF THE INVENTION

The invention relates to apparatuses and methods for treatment of conditions directly or indirectly causing dysfunction of neural tissue. More specifically, the invention relates to apparatuses and methods for modulating the function of particular structures and tissues for treatment of sudden neurological dysfunction.

BACKGROUND

Among other pathophysiological processes, loss of adequate blood flow to part or all of the central nervous system (brain and spinal cord) and electrochemical irregularity in the central nervous system can cause sudden neurological dysfunction.

One example of sudden neurological dysfunction caused by the reduction of blood flow to the central nervous system is a cardiac arrhythmia that dyscoordinates heart contraction, reducing cardiac output and decreasing blood pressure. Arrhythmia of significant severity can lead to cessation of brain activity; if it is persistent and not promptly reversed, it can cause death. In emergency situations, the most commonly-employed means of reversing severe cardiac arrhythmia is defibrillation, a treatment that acts by delivering an electrical current to the heart. Electrodes applied to the chest or to the heart directly or through a transvascular approach are used to deliver electrical current to the heart. The patient is typically unresponsive at the time.

Another example of sudden neurological dysfunction caused by a blood flow abnormality is stroke, during which blood flow to the brain is disrupted either by occlusion of a cerebral artery (ischemic stroke) or by rupture of a cerebral artery (hemorrhagic stroke). Either type of stroke can cause sudden neurological dysfunction that is typically focal in nature and that often does not involve the loss or even impairment of consciousness or alertness. Ischemic stroke can be treated with intravenous enzymes that dissolve blood clots or by endovascular catheter devices that can physically disrupt or retrieve blood clots. Hemorrhagic stroke is typically treated using endovascular catheter devices or neurosurgical procedures to repair the ruptured artery.

An example of sudden neurological dysfunction that can be, but is not necessarily, triggered by a blood flow abnormality is seizure. During seizure, a portion or multiple portions of the central nervous system develop abnormal patterns of electrical activity, typically in which groups of neurons of the cortex become active in synchrony. Seizure in the emergency setting is typically treated with medications that act to sedate or desynchronize the activity of the abnormally-coordinated neurons.

By causing global ischemia of the central nervous system, cardiac arrhythmia can induce stroke and/or seizure activity in the acute setting by causing brain damage. Conversely, patients with focal brain damage from stroke or seizure can be unresponsive, and this can resemble cardiac dysfunction. The coincidence and symptomatic similarities of these conditions complicates the emergency diagnosis and treatment of a patient with sudden neurological dysfunction, particularly when one considers the worsened likelihood of survival and quality of clinical outcomes from delayed treatment of these time-dependent conditions.

Unlike cardiac arrhythmia, stroke and seizure are not known to be responsive to direct stimulation of the affected organ, i.e., the brain. However, selective stimulation of certain neural systems may influence stroke and seizure in a therapeutic manner. For example, some cranial and peripheral nerves (e.g., the trigeminal and facial nerves) appear to regulate the size of, and blood flow through, brain arteries. Also for example, some cranial and peripheral nerves (e.g., the vagal nerve) appear to regulate the excitability of neurons in the cerebral cortex that are prone to developing epileptiform activity consistent with seizures. In the latter case, an implantable vagal nerve stimulator has been studied and approved for use in the prevention of seizures in patients with epilepsy. To date, no stimulator device has been approved for the emergency treatment of stroke, although such devices are in development.

SUMMARY

Accordingly, disclosed herein is a medical device and method-of-use of the medical device that can treat multiple causes of sudden neurological dysfunction simultaneously, or serially, as needed by the patient. The device is capable of delivering electrical current for management of disorders of the heart's conduction system such as ventricular tachycardia or fibrillation. The device is simultaneously capable of delivering pulsed magnetic stimulation to one or more non-cardiac tissues that are capable of being depolarized by induced electrical current, such as cranial or peripheral nerves, for the purpose of inducing cerebral artery dilation or reducing excitability of the cerebrum. In some embodiments, the device is equipped with a user interface capable of determining the need for cardiac stimulation and/or stimulation of non-cardiac depolarizable tissues based on limited input from sensors, the device user, or the patient.

DETAILED DESCRIPTION

Apparatuses and methods-of-use are provided for the treatment of two major categories of sudden neurological dysfunction in the general population:
 focal neurological dysfunction, including that caused by ischemic stroke, hemorrhagic stroke, and/or seizure, wherein the neurological injury may be considered to be a direct effect of abnormalities in the neurovasculature or neural parenchyma;
 global neurological dysfunction caused by cardiac output failure such as that resulting from arrhythmia, wherein the neurological injury may be considered an indirect consequence of the cardiovascular failure.

The apparatus acts to deliver appropriate energies to select neural structures, or component thereof, for the treatment of focal neurological conditions and to the heart for the treatment of global neurological conditions. The combination of stimulations and their order of delivery are determined by the patient's need.

Neural structures of interest in this regard include the oculomotor, trigeminal, facial, glossopharyngeal, and vagal nerves, sympathetic structures, as well as other nerves with autonomic or sensory function. The facial nerve system includes, but is not limited to, the facial nerve, the geniculate ganglion, the tympanic plexus, the sphenopalatine nerves and ganglion, tympanic plexus, the intermediate nerve, the vidian nerve, and the petrosal nerves. More generally, neural structures also can include other cranial nerves, peripheral nerves, ganglia, paraganglia, and central nervous system structures.

Arrhythmias treated by the device include those caused by dysfunction of heart tissues including electrically-conductive tissues controlling the heart (e.g., sinoatrial or atrioventricular nodes, internodal pathways, bundle branches, Purkinje cells) and/or contractile/muscular/myocardial tissues.

In this description, the term 'stimulation' implies energy delivery to a tissue for the purpose of increasing, decreasing, or otherwise modulating a functional property of that tissue or a related tissue. Stimulation energy may be in the form of electromagnetism, ultrasound, radiofrequency, thermal, or photonic energies.

Figure 1:
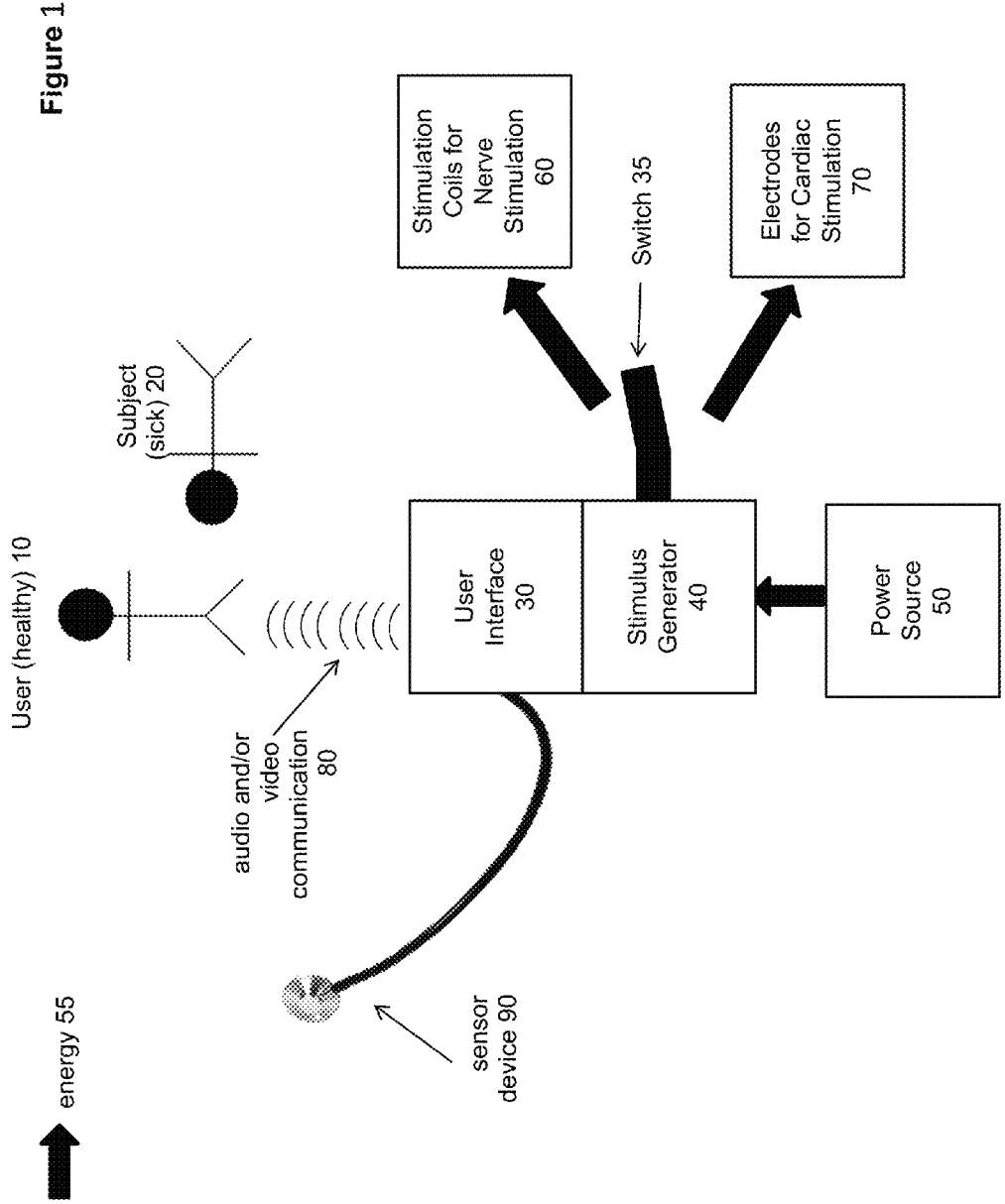
FIG. 1 includes a block diagram of a device that is capable of serial direction of energy from a stimulus generator to different types of end devices that, in this example, are configured to deliver electrical stimulation to the heart and magnetic stimulation to a cranial or peripheral nerve.

FIG. 1 is a block diagram of a device that is capable of serial direction of energy from a stimulus generator to different types of end devices, according to one embodiment. Such end devices, for example, are configured to deliver electrical stimulation to the heart, magnetic stimulation to a cranial or peripheral nerve, or a combination thereof. As shown in FIG. 1, the device includes a power source 50, stimulus generator 40, user interface 30, stimulation coils for nerve stimulation 60, electrodes for cardiac stimulation 70, switch 35, sensor device 90, and communication 80. The device can be used by a trained professional user (e.g., user 10, who could be a doctor or nurse) either in the hospital or patient care environment or out in the field to administer treatment to a subject (e.g., subject 20). The device can be also used by an untrained user (e.g., user 10) following instructions provided by the device to provide treatment to another user (e.g., user 20).

In operation, power source 50 sends energy 55 to a stimulus generator 40 that is alternately coupled directly or indirectly to one of two types of end devices capable of delivering stimulation energy to a tissue, depending upon the intended use to treat a condition of focal neurological dysfunction or a condition of global neurological dysfunction in a single subject 20 (FIG. 1). For treatment of focal conditions of the subject 20, the end device is one or more magnetic field generators 60 (alternatively referred to herein as stimulation coils for nerve stimulation 60) that interact non-invasively with a cranial or peripheral nerve for a desired physiological effect, such as enlargement or widening of a cerebral, carotid, or cranial artery, or the opening of a connection between such arteries (collateral arteries). Generation of the electromagnetic field(s) in one such embodiment of the apparatus may be accomplished by electrically-conductive wire arranged as a loop or other geometric shape ("coils") wherein the electrically-conductive wire is not in direct contact with the subject but is placed against a surface of the subject.

The end device 60 can be configured in various manners. In some embodiments, the end device (e.g., magnetic field generator 60) is a stimulating device that causes dilation (e.g., relaxation) of the cerebral arteries, for example, by approaching or being placed in the vicinity of the facial nerve and branches of the facial nerve as they pass through and near to the ear. Other embodiments place the end device in the face or exterior to the skull. In one embodiment, the end device or a portion of the end device can be inserted into the ear canal and is configured to stimulate the facial nerve system using stimulating energy such as a magnetic field. Alternatively, the end device can be advanced into the middle ear through an incision created in the ear drum, and branches of the facial nerve in the middle ear can then be directly stimulated by application of electrical current. As yet another embodiment, the end device is configured to be placed outside and in proximity to the ear, over the pinna, concha, scapha, tragus, or antitragus of the external ear (e.g., in the form of a wearable ear piece or headset or in the form of a headrest). The end device could similarly be placed at another location of the subject's head from which the facial nerve system can be stimulated, such as within the mouth or nasal spaces.

The end device optionally includes a coil with a pair of elongated ends, the coil having an insulating guide sheath. Current provided to and flowing through the coil is optionally used to stimulate or activate a neural structure of the facial nerve system (e.g., by generation of a stimulating magnetic field). In some embodiments, a frequency of alternating current provided to the coil ranges from 0.01 to 100 Hz; a current of 0.1 to 5.0 mA; a magnetic field strength ranges from 0.01 to 5.0 Tesla; the current or stimulus waveform is a biphasic or oscillatory waveform with or without a delay between the phases. In some embodiments, the coil has an outer diameter of less than 6 mm, an inner diameter of at least 2 mm, and a length of 10-30 mm. In some embodiments, the coil is coiled into 5-25 layers with 50-250 turns per layer. In some embodiments, the stimulating magnetic field is applied intermittently or periodically. Various end devices and methods for providing electrical stimulation energy, magnetic stimulation energy, or a combination thereof, to stimulate to the facial nerve system are further described, for instance, in U.S. patent application Ser. No. 13/096,889 entitled "Modulating Function of the Facial Nerve System or Related Neural Structures via the Ear" filed on Apr. 28, 2011, and in U.S. patent application Ser. No. 13/692,226 entitled "Modulating Function of Neural Structures Near the Ear" filed on Dec. 3, 2012, both of which are incorporated herein by reference in their entireties.

For treatment of global conditions of the subject 20, in some embodiments, the end device comprises a plurality of electrodes 70 that deliver electrical current to the thorax of the subject in a manner that influences the electrical activity of the heart (e.g., by temporarily blocking or interrupting the irregular depolarization-repolarization cycle and allowing for electrical repolarization of cardiac tissues). The electrode(s) 70 used to treat global neurological dysfunction conditions are otherwise similar to those used in cardiac defibrillators/external automated defibrillators/cardioversion devices. In such embodiments, the stimulus generator 40 provides stimulation energy to the electrodes 70 for delivering a therapeutic dose of electrical energy to the heart sufficient to depolarize or hyperpolarize a critical mass of the heart muscle, terminate a dysrhythmia, and/or allow normal sinus rhythm to be reestablished by the body's natural pacemaker (the sinoatrial node of the heart). The stimulus generator 40 optionally provides a charge that is delivered to the patient and generated by high voltage generation circuits from energy stored in a capacitor bank (e.g., internal to the stimulus generator 40) that can hold up to 7 kV of electricity.

The electrodes 70 are optionally made from titanium and silicone rubber and are configured to make electrical contact with the chest or torso of the subject and deliver electrical energy (from the stimulus generator 40) to the chest or to the torso. Electrodes 70 are optionally configured to be handheld paddles, internal paddles, and self-adhesive electrodes, pre-gelled disposable electrodes, or any other suitable configuration of electrodes. In some embodiments, stimulus generator 40 provides electrical stimulation to electrodes 70 based on one or more of the following parameters: stimulus energy ranging from 30-400 joules; pressure with which the electrodes 40 are applied to the torso is approximately 25 lb. (11 kg); biphasic, biphasic truncated, or monophasic stimulus waveforms with a waveform duration lasting 5-20 msec. Various other devices and methods for providing electrical stimulation energy to stimulate or defibrillate the heart are further described, for instance, in Clinical Cardiac Pacing and Defibrillation, 2nd Edition (Ellenbogen K A, Kay G N, Wilkoff B L, eds. WB Saunders, 2000), which is incorporated herein by reference in its entirety. The features of these devices and methods can also be incorporated into the devices and methods described in this application.

In the embodiment shown in FIG. 1, the nature of the stimulation energy (voltage, current, duration of flow, waveform shape, etc.) coming from the stimulus generator is then determined by the type of condition to be treated in the subject 20. Stated differently, the stimulus generator 40 is configured to select (e.g., select automatically, select based on patient 20 or user 10 intervention, or select based on one or more patient parameters measured via sensors 90) one or more attributes or parameters of the stimulation energy to be delivered to the magnetic field generators 60, electrodes 70, or both. In some embodiments, it may be preferably to electrically isolate one end device while the other is being employed. It should be understood that the voltage, current, values duration of current pulsation, waveform shapes, and the like, described herein are merely illustrative and representative; the device and methods performed by the device described herein can be configured to operate at parameter values not specifically listed here.

In some embodiments, an interactive user interface 30 guides the selection of the end device to be applied to the subject 20 by a user 10 according to audio and/or visual instructions and feedback 80 in a question/answer format obtained from a healthy user 10 of the device. In some embodiments, the interactive user interface 30 is configured to actively query the user 10 (and/or subject 20 if the subject is conscious and able to respond) with regard to the subject's physical state or disposition (e.g., level of hydration, interval or time lapse since a last meal, duration of sleep over the past week, preexisting diagnosis of diabetes, and the like), presence and acuity of specific symptoms (e.g., fatigue, pain in the chest or neck, shortness of breath, head ache, dryness in the mouth, sudden vision defects such as blurry vision, and the like). Alternatively, or in addition, the interactive user interface 30 is configured to allow the user (user 10 and/or subject 20) to input symptoms and other information without a prompt from the device.

In some embodiments, the communication 80 may be bidirectional or interactive. In other embodiments, the communication 80 may involve telecommunication of the user 10 with remote healthcare providers (not shown) who can guide use of the device and other treatments. For example, a remote physician has the capability to interact with the user 10, via the communication 80, to instruct the user 10 on locations of placement of magnetic field generators 60, electrodes 70, or both. Alternatively, a remote nurse has the ability to monitor one or more parameters or vital signs (measured by sensors 90) of the subject 20 and provide real-time feedback to the user 10 via communication 80 to administer or modify the one or more parameters of stimulation energy being provided to magnetic field generators 60, electrodes 70, or both. Alternatively, in some embodiments, the remote healthcare provider directly provides control instructions for activation of stimulus energy or for the modification of the one or more parameters of stimulation energy being provided to magnetic field generators 60, electrodes 70, or both.

In other embodiments, the selection of the end devices to be applied to a subject 20 is determined entirely or in part by measures derived from one or more sensors 90 that inform the user interface 30 that then controls the output of the stimulus generator 40. In some embodiments, sensors 90 include sensors that measure blood oxygen concentration (e.g., pulse oximeters or photoplethysmography), blood pressure, heart rate or pulse rate, or QRS complex shape (e.g., electrocardiographs, impedance cardiographs), mechanical activity of the heart (e.g., echocardiography sensors), heart sounds (e.g., phonocardiographic sensors), respiratory function (e.g., respiration belts, spirometers, etc. for the measurement of respiration rate, volume, effort, periodicity, and so on) and the like. Additional sensor technologies include impedance spectroscopy, ultrasound/laser Doppler, infrared, or optical sensing for the detection of blood suffusion, tissue volume, blood flow velocity, or local heating in superficial or ocular tissue. Other body vitals or parameters optionally measured by sensors 90 include: carotid, cerebral, or cranial artery blood flow; nerve electrical potentials; skin/scalp galvanic responses or conductances; skin/scalp blood flow; blood pressure or pulsation; oral or lacrimal secretion; ear temperature; pupilometry and pupil size assessment; intraocular pressure; bioelectric potentials including electrocardiography or electroencephalography. In such embodiments, one or more of the different types of end devices are selected for the treatment of conditions causing focal and global neurological damage, in part, based on one or more of these measures derived from a sensor 90. In some embodiments, the end devices themselves are used to assess these parameters or body vital measurements, such as the measurement of electrocardiographic potentials to determine heart rate or cardiac rhythm and so on.

In such embodiments, the device (e.g., the user interface 30) determines (e.g., based on one or more vital signs or other patient parameters measured by sensors 90, or provided by a user 10 or the subject 20) which type of end device is to be applied to the subject 20, and informs via communication 80 the user 10 to apply the selected or appropriate end device type to the subject 20. Once the nature of the subject's medical problems are determined, the type of end device can be selected (e.g., the magnetic field generators 60, the electrodes 70, or some combination thereof) and the type of energy necessary to drive or power the necessary end device can be sent or directed to that end device by means of a controllable switch 35.

Figure 2:
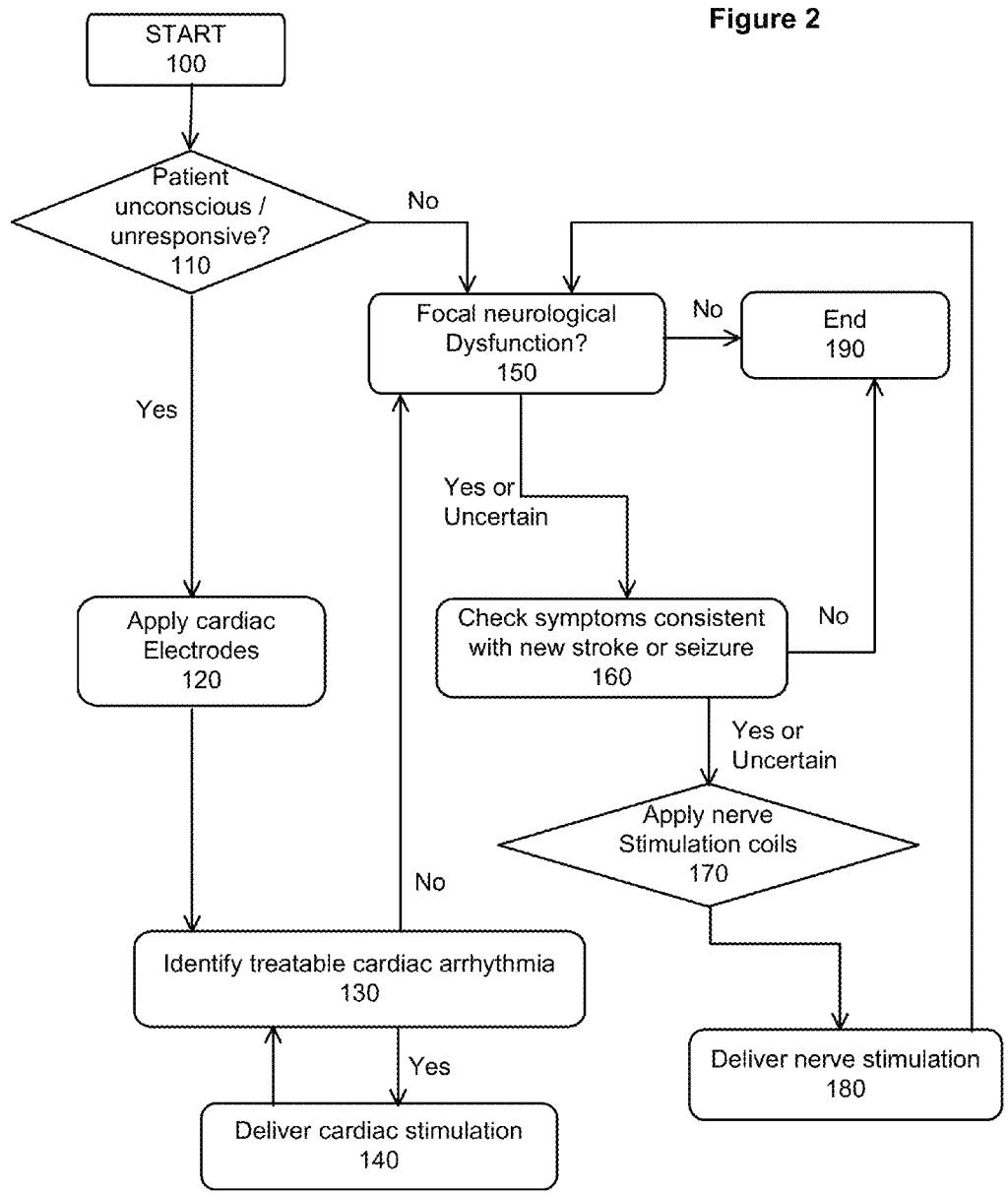
FIG. 2 includes a flowchart for use a device such as that shown in FIG. 1, in which sudden neurological dysfunction (e.g., arising from potentially multiple distinct causes) is assessed and treated. In some embodiments, such treatment is serial—for example, first by cardiac defibrillation (e.g., to restore cardiac rhythm or other cardiac function) and subsequently by stimulation of cranial or peripheral nerves (e.g., to reverse stroke or interrupt seizure activity).

For example, if the device is informed by a user 10 that a subject 20 is unconscious without known cause or history (per step 110 of FIG. 2), and if the device detects a wide QRS complex EKG potential (e.g., via a suitable sensor 90 such as an electrode, per step 120 of FIG. 2) in excess of 100 beats per minute, the device determines that subject 20 has a treatable cardiac arrhythmia (per step 130 of FIG. 2) such as ventricular tachycardia or ventricular fibrillation/flutter, then selects the appropriate end device (in this case, cardiac defibrillation pads 70) and determines a specified set of attributes or parameters for stimulus energy released from the stimulus generator 40 to be provided to the selected end devices, according to their intended use to defibrillate the heart (per step 140 of FIG. 2).

On the other hand, if the device is informed by a user 10 that a subject 20 is unconscious (per step 110 of FIG. 2) without known cause or any history, and if the device detects a narrow QRS complex EKG potential (e.g., via a suitable sensor 90 such as an electrode, per step 120 of FIG. 2) in conjunction with a pulse (e.g., via pulse oximetry or other suitable sensor 90), the device determines that subject 20 does not have a treatable cardiac arrhythmia (per step 130 of FIG. 2), then selects the appropriate end device (in this case, magnetic field generator 60) and determines a specified set of attributes or parameters for stimulus energy released from the stimulus generator 40 (e.g., a current value ranging from 4000-6000 A; a current duration 200-300 µsec; and the like) to be provided to the selected end device intending to stimulate neural structures capable of dilating the arteries of the brain, for example, the trunk of the facial nerve to address the detected neural condition (per steps 150-180 of FIG. 2).

In some embodiments, an interactive user interface 30 provides audio and/or video guidance 80 as to the use of sensors 90 for identification of conditions causing localized and/or diffuse disruption of normal neural function.

In some embodiments and methods-of-use, cranial and peripheral nerve stimulation end devices are employed so as to improve the effectiveness of end devices applied to stimulate the heart. An example of such use is to maximize the restoration of cerebral blood flow by coordinated stimulation of nerves that dilate the cerebral arteries and provide cardiac defibrillation. As described above, neurological dysfunction and cardiac dysfunction can be causally linked and may coexist. For example, on the one hand, reduction of blood flow to the central nervous system or electrical malfunction of the brain can cause a cardiac arrhythmia; and on the other hand, cardiac arrhythmia can induce stroke and/or seizure activity. Under such circumstances, symptoms of neurological dysfunction and cardiac dysfunction may simultaneously co-occur and be measurable in the patient's vital signs or other diagnostic testing. Accordingly, in some embodiments, the two methods of treatment are administered concurrently or substantially concurrently (e.g., alternating rapidly or alternating in quick succession or cyclically), for example, to reinforce or augment the overall effect on the patient by simultaneously stimulating both the nervous and cardiovascular systems as opposed to any single form of treatment being administered at a given time. Alternatively, or in addition, patient symptoms are further analyzed or evaluated to identify symptoms that indicate a likely cause among the coexisting conditions—neurological dysfunction and cardiac dysfunction. For example, a specific symptom appearing only on one side of the body or in one limb may indicate that reduction of blood flow to the central nervous system caused a cardiac arrhythmia; whereas a set of vital sign measurements such as an increased heart rate/tachycardia and/or an abnormally shaped QRS EKG complex (i.e., wide, irregular, or lacking certain component potentials) may indicate that cardiac arrhythmia induced stroke and/or seizure activity. In such embodiments, responsive to identifying the likely cause, treatment is more heavily favored or targeted toward that cause. For example, if the symptoms indicate that cardiac arrhythmia and stroke coexist, but the symptoms were caused by cardiac arrhythmia, the stimulation is more heavily directed or favored toward the electrodes 40 (for treatment of the arrhythmia) such as for a longer duration of time or more stimulation trials than toward magnetic field generator 60 (for treatment of stroke)—although both treatments may be provided simultaneously.

With some embodiments and methods-of-use, use of nerve-activating end devices may be appropriate to treat disorders of the cerebrovascular circulation (stroke, chronic cerebrovascular atherosclerosis), head trauma, headache disorders, or other neurological conditions. With some embodiments and methods-of-use, use of the nerve stimulation end devices may be appropriate prior to procedures that involve the cerebral and carotid arteries, such as endovascular clot retrieval during stroke, endovascular coil and stent placement in subarachnoid hemorrhage, diagnostic angiography, or surgical carotid endarterectomy. In some embodiments, use of nerve stimulation end devices may interrupt seizure activity, reduce the likelihood of developing a seizure, or prevent the development of epilepsy. In some embodiments, use of cranial and peripheral nerve stimulation end devices may reduce inflammation within or of the head, neck, and/or elsewhere in the body. In some embodiments and methods-of-use, stimulation of cranial and peripheral nerves may reduce blood flow to the brain and head, for example, when used to treat head trauma, headache, or hemorrhagic stroke (intracerebral, subarachnoid, or subdural hemorrhage).

FIG. 2 includes a flowchart for use of a device such as that shown in FIG. 1, in which sudden neurological dysfunction (e.g., arising from potentially multiple distinct causes) is assessed and treated. In some embodiments, such treatment is serial—for example, first by cardiac defibrillation (e.g., to restore cardiac rhythm or other cardiac function) and subsequently by stimulation of cranial or peripheral nerves (e.g., to reverse stroke or interrupt seizure activity).

As shown in FIG. 2, use of the device described in FIG. 1 in an emergency setting can involve an initial assessment of the patient's level of responsiveness/consciousness/arousal 110 after discovering the patient 100 in a sick condition. This assessment may depend upon interaction of the user of the device and the patient or, in some embodiments, an action of the device upon the patient. Significant cardiac arrhythmia is likely to cause unresponsiveness/ unconsciousness/inarousability, therefore in such a patient the device use flowchart can involve application of electrodes to the chest of the subject 120 in a manner that allows them to detect the electrical conduction potential of the heart (i.e., the electrocardiogram). Internal analysis of the electrocardiogram performed by the device 130 then determines the need to deliver, or potential benefit of delivering, stimulation energy to the heart 140 as a means to interrupt the activity of the cardiac excitable tissues, resetting the heart rhythm; this can be accomplished though the electrocardiogram-sensing electrodes or through a different set of stimulator devices. In some embodiments, cardiac stimulation must be regularly delivered on a continuous basis as a means of inducing repeated heart contractions (i.e., pacemaking the heart).

In the event that a cardiac arrhythmia is not adequately treated by a first delivery of energy to the heart, the method-of-use shown in FIG. 2 allows for repeated stimulation of the heart until the cardiac rhythm is improved. After achieving a stable cardiac rhythm, the patient is again assessed, but this time for focal neurological dysfunction 150. This assessment may be directed by a user of the device and/or by direct interaction of the device and patient. If evidence of focal neurological dysfunction such as partial visual field loss or vision loss, gaze dysconjugation or diplopia, convulsions, uncontrolled movements, confusion, difficulty with language or speech production, or severe headache is identified that is consistent with an acute seizure or stroke 160, the end devices appropriate for stimulation of desired cranial or peripheral nerves are applied to the relevant part of the body 170. The nerves selected for stimulation, and the relevant part of the body to which the end devices are applied, are determined based on the physiological responses expected by stimulation of those nerves. In this embodiment, the nerves are then stimulated 180 so as to interrupt ongoing seizure activity, improve blood flow to an ischemic area of the brain, or to reduce brain injury caused by hemorrhagic stroke or intracerebral hemorrhage. Repeated nerve stimulation may be justified or completion of a single stimulation may end 190 the intervention with the device. In some embodiments, uncertainty around the presence of focal neurological dysfunction 150 or its relation to stroke or seizure 160 allows for the application 170 or use 180 of nerve stimulation to treat the patient.

Figure 3:
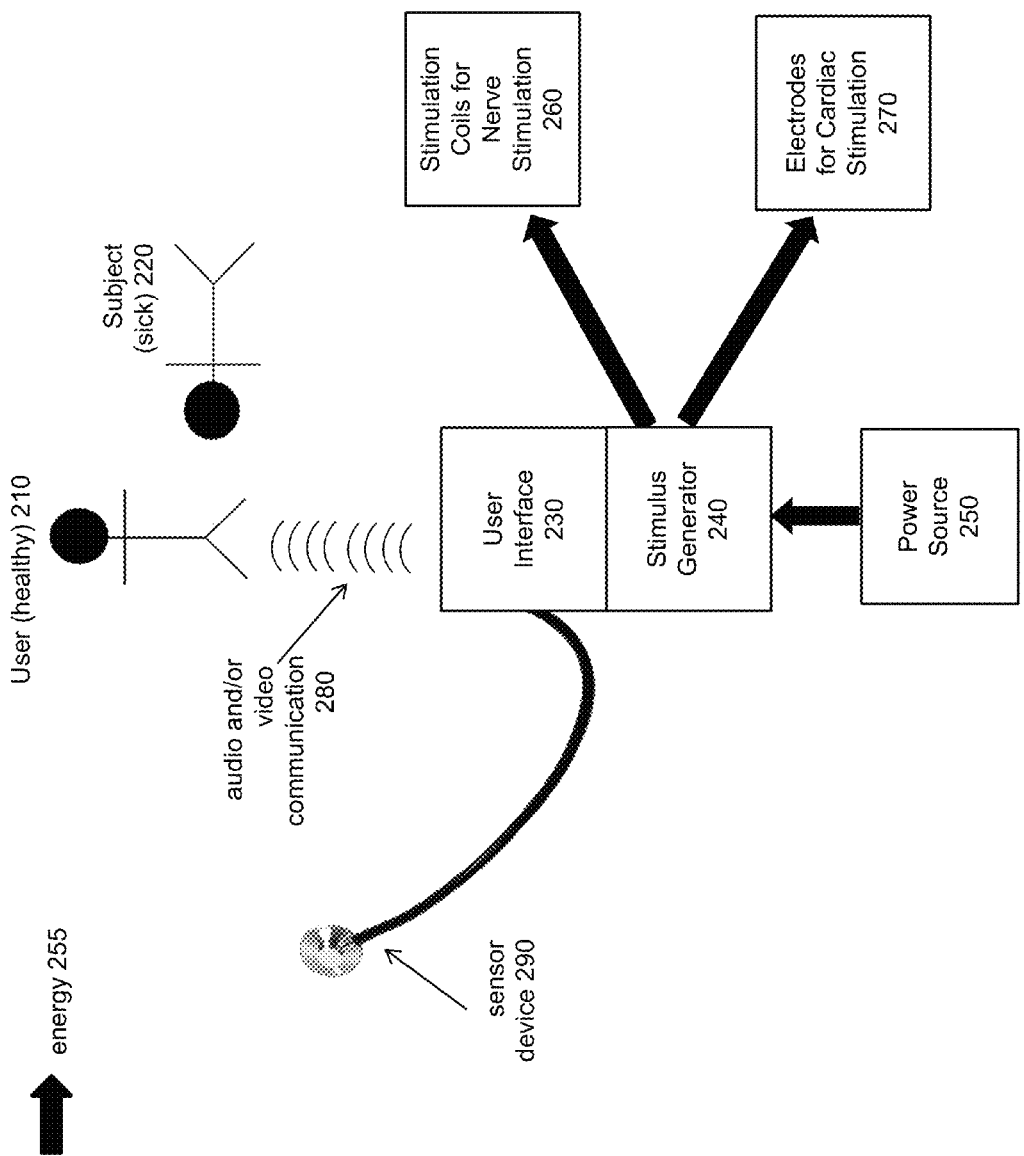
FIG. 3 includes a schematic of a device that is capable of simultaneous direction of energy from a stimulus generator to different types of end devices that, in this example, are configured to deliver electrical stimulation to the heart and magnetic stimulation to a cranial or peripheral nerve.

FIG. 3 includes a block diagram of a device that is capable of simultaneous direction of energy from the stimulus generator to different types of end devices. Such end devices, for example, are configured to deliver electrical stimulation to the heart, magnetic stimulation to one or more cranial or peripheral nerves, or a combination thereof. As shown in FIG. 3, the device includes a power source 250, stimulus generator 240, user interface 230, stimulation coils for nerve stimulation 260, electrodes for cardiac stimulation 270, sensor device 290, and communication 280. In some embodiments, power source 250, stimulus generator 240, user interface 230, stimulation coils for nerve stimulation 260, electrodes for cardiac stimulation 270, sensor device 290, and communication 280 of FIG. 3 share one or more properties or attributes, respectively, of power source 50, stimulus generator 40, user interface 30, stimulation coils for nerve stimulation 60, electrodes for cardiac stimulation 70, sensor device 90, and communication 80 described above with reference to FIG. 1. For brevity, these details are not repeated here.

As shown in FIG. 3, another general design for the invention hardware allows for simultaneous stimulation of the heart and non-cardiac tissues. A user 210 who encounters a sick subject 220 can employ the device and support its use through audio and/or video communication 280 with a user interface 230 for the purpose of applying two types of end devices to the subject 220. In one embodiment, the end devices are stimulation coils for nerve stimulation 260 and electrodes for cardiac stimulation 270, which have individual connections to a stimulus generator 240 that is supplied with electricity from a power source 250. Sensor devices 290 applied to the subject 220 may modify the instructions 280 provided by the user interface 230 to the user 210 or lead to alteration of the delivery of energy 255 to the end devices.

Other methods-of-use of the device described in FIG. 3 involve simultaneous cardiac and nerve stimulation. As described with reference to FIG. 1 above, in some embodiments, when patient symptoms that are likely to indicate a coexistence of neurological dysfunction and cardiac dysfunction are detected, responsive to detecting the presence of these symptoms, the two methods of treatment are administered concurrently or substantially concurrently (e.g., alternating rapidly or in quick succession or alternating with high frequency). Simultaneous or substantially simultaneous stimulation of both the cardiac and nervous systems reinforces the overall diagnostic or therapeutic effect on the patient compared to any single form of treatment being administered at a given time. In one example, this would be done so as to restore blood flow to the brain with increased speed and magnitude, namely by restoring heart contractility while dilating the arteries supplying the brain.

As described above with reference to FIG. 1, if the device is informed by a user 210 that a subject 220 is unconscious without known cause or history, and if the device detects a wide QRS complex EKG potential (e.g., via a suitable sensor 290 such as an electrode) in excess of 100 beats per minute, the device determines that subject 220 has a treatable cardiac arrhythmia such as ventricular tachycardia or ventricular fibrillation/flutter, then selects the appropriate end device (in this case, cardiac defibrillation pads 270 and magnetic field generator 260) and determines a specified set of attributes or parameters for stimulus energy released from the stimulus generator 240 to be provided to the selected end devices, according to their intended use to defibrillate the heart or to stimulate neural structures capable of dilating the arteries of the brain.

Figure 4:
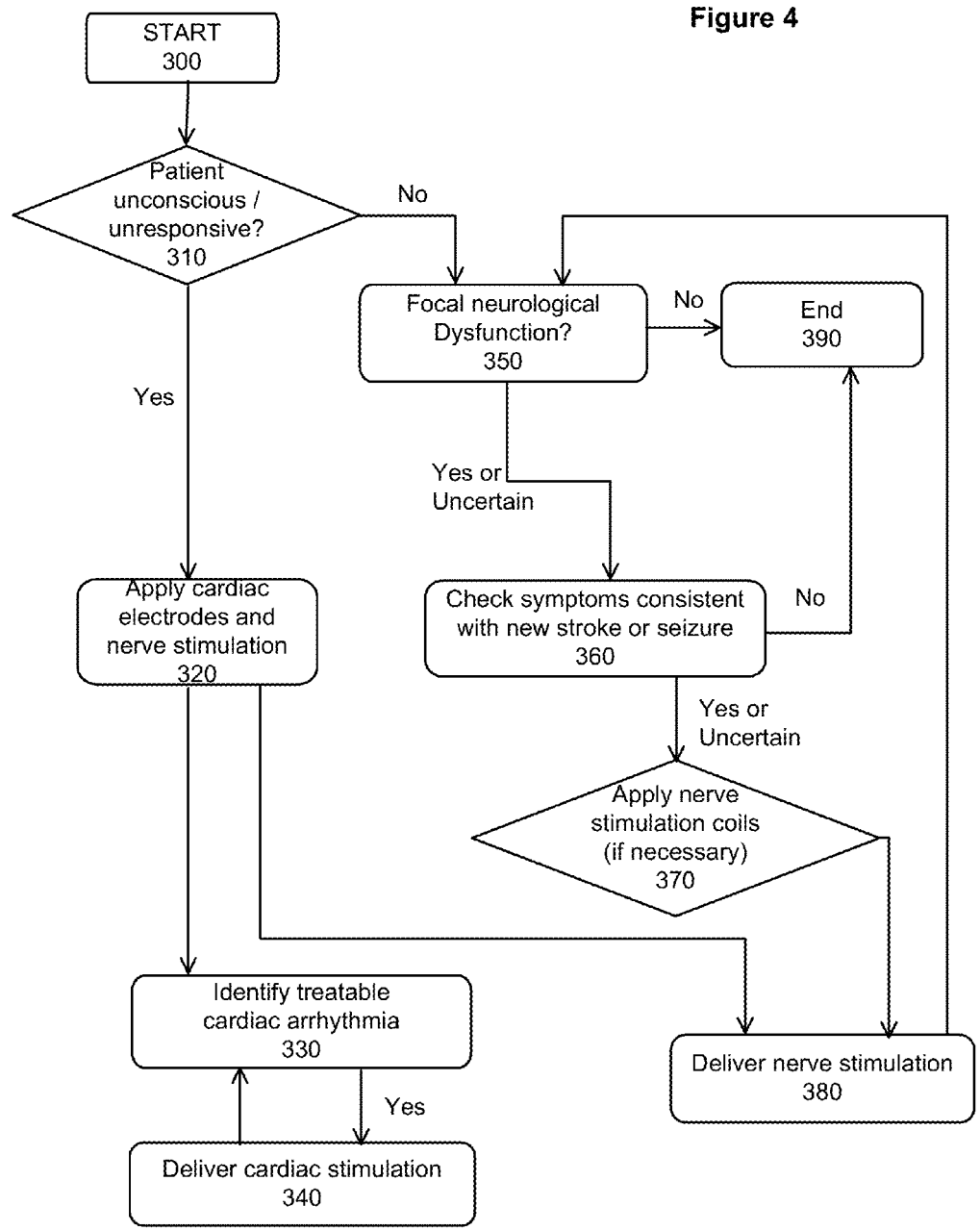
FIG. 4 includes a flowchart for use of a device such as that shown in FIG. 3, in which sudden neurological dysfunction caused by cardiac arrhythmia is simultaneously treated with stimulation of cranial or peripheral nerves, but in which nerve stimulation can be administered without cardiac stimulation in appropriate subjects who do not exhibit cardiac dysfunction.

FIG. 4 includes a flowchart for use of a device such as that shown in FIG. 3, in which sudden neurological dysfunction caused by cardiac arrhythmia is simultaneously treated with stimulation of cranial or peripheral nerves, but in which nerve stimulation can be administered without cardiac stimulation in appropriate subjects.

As represented in FIG. 4, a newly discovered person found to be unconscious 310 is first evaluated by placement of sensor devices capable of detecting a cardiac hypodynamic state (e.g., arrhythmia, hypotension), and at the same time end devices capable of delivering energy to cardiac and a desired non-cardiac neural structure such as a cranial or peripheral nerve or ganglion are applied to the person 320. Stimulation energy may include pulsed magnetic energy, ultrasonography energy, thermal energy, and/or radiofrequency energy, depending upon the need and the structure of the end device. If an arrhythmia is detected through an appropriate evaluation 330, stimulation energy is delivered through the thoracoabdomen to overcome or adjust the cardiac activity 340. At that time (e.g., simultaneous with), or without significant delay, stimulation energy is also delivered to the target non-cardiac neural structure 380. In the example shown in FIG. 4, the cardiac hypodynamic state is an arrhythmia and the sensor device is an electrocardiogram electrode that is also capable of delivering stimulation energy.

According to this method-of-use, if no cardiac dysfunction is found in the unconscious person 330, stimulation is still delivered to the neural structures 380 under the assumption that the unconscious state is caused by seizure or stroke. In other causes of sudden unconsciousness, this treatment would not be harmful and would be safe to administer.

In the method-of-use described in FIG. 4, if the sick person is not unconscious 310 upon initial evaluation, or if the sick person was unconscious due to heart arrhythmia but was successfully resuscitated by cardiac stimulation 340, the person is then evaluated for focal neurological dysfunction 350, for example, that is consistent with stroke or seizure. This can be done by the user acting under the request of the user interface, by direct interaction of the user interface with the sick person, and/or by sensor devices applied to the sick person. If evidence is found indicating the presence of treatable focal neurological dysfunction (in this example, sudden-onset clumsiness, ataxia, facial asymmetry or other symptom caused by stroke or seizure 360), energy necessary for appropriate neuromodulation is delivered only toward the relevant non-cardiac neural structure through the end device, here stimulation coils 370 and 380. In this example, repeated stimulation may be warranted depending upon the responsiveness of the sick person to stimulation of the non-cardiac neural structure or until stimulation is known to be no longer effective, thereby ending 390 the person's treatment.

An additional cause of unconsciousness due to cardiac failure is asystole or pulseless electrical activity, in which defibrillation would be unlikely to be effective and in which chest compression (cardiopulmonary resuscitation [CPR]) is typically administered. Another embodiment of the present invention replaces or complements end devices used for cardiac defibrillation such as electrical paddles with chest compression devices that act by anterior-posterior compression or other constriction of the thoracoabdomen as a means to compress the heart and cause forward flow of blood throughout the body. The methods-of-use of such a device is otherwise as per FIG. 2 or FIG. 4, with the exception that cardiac electrodes are not employed, but rather a mechanical means of increasing intrathoracic pressure or compressing the rib cage is employed.

In some embodiments, the treatment of a cardiac arrhythmia such as a ventricular tachycardia may be treated first by stimulation of a cranial or peripheral nerve in an attempt to interrupt or slow the heart rhythm, or otherwise to reduce the excitability of heart tissue prior to or in combination with direct cardiac stimulation. In this use, stimulation of the non-cardiac neural structure interrupts the arrhythmia and allows a normal heart rhythm to develop, or else predisposes the heart to effective therapies, e.g., by changing heart tissue sensitivity to defibrillation or to pharmacological agents. In some embodiments, such treatment involves magnetic stimulation of the vagus nerve, which has a parasympathetic autonomic property to slow heart rate by inhibition of the sinoatrial and/or atrioventricular nodes of the heart. In some methods of use of these embodiments, the stimulation is delivered in conjunction with stimulation of a cranial or peripheral nerve such as the facial nerve that causes dilation of the arteries of the head. In some embodiments, a single stimulation coil or assembly of coils is of sufficient size, shape, and placement on the body so that it is capable of stimulating both cranial nerves in the base of the skull (e.g., the facial nerve) and cranial nerves running through the neck (e.g., the vagus nerve) simultaneously. In other embodiments, a single stimulation coil or assembly of coils is capable of stimulating the facial, vagus, and phrenic nerves, the phrenic nerve stimulation serving to drive movements of the respiratory musculature/diaphragm. Failure of such stimulation that includes stimulation of the vagus nerve to induce an improvement in the cardiac rhythm may then necessitate direct electrical stimulation of the heart with different end devices, e.g., electrical current paddles.

Figure 5:
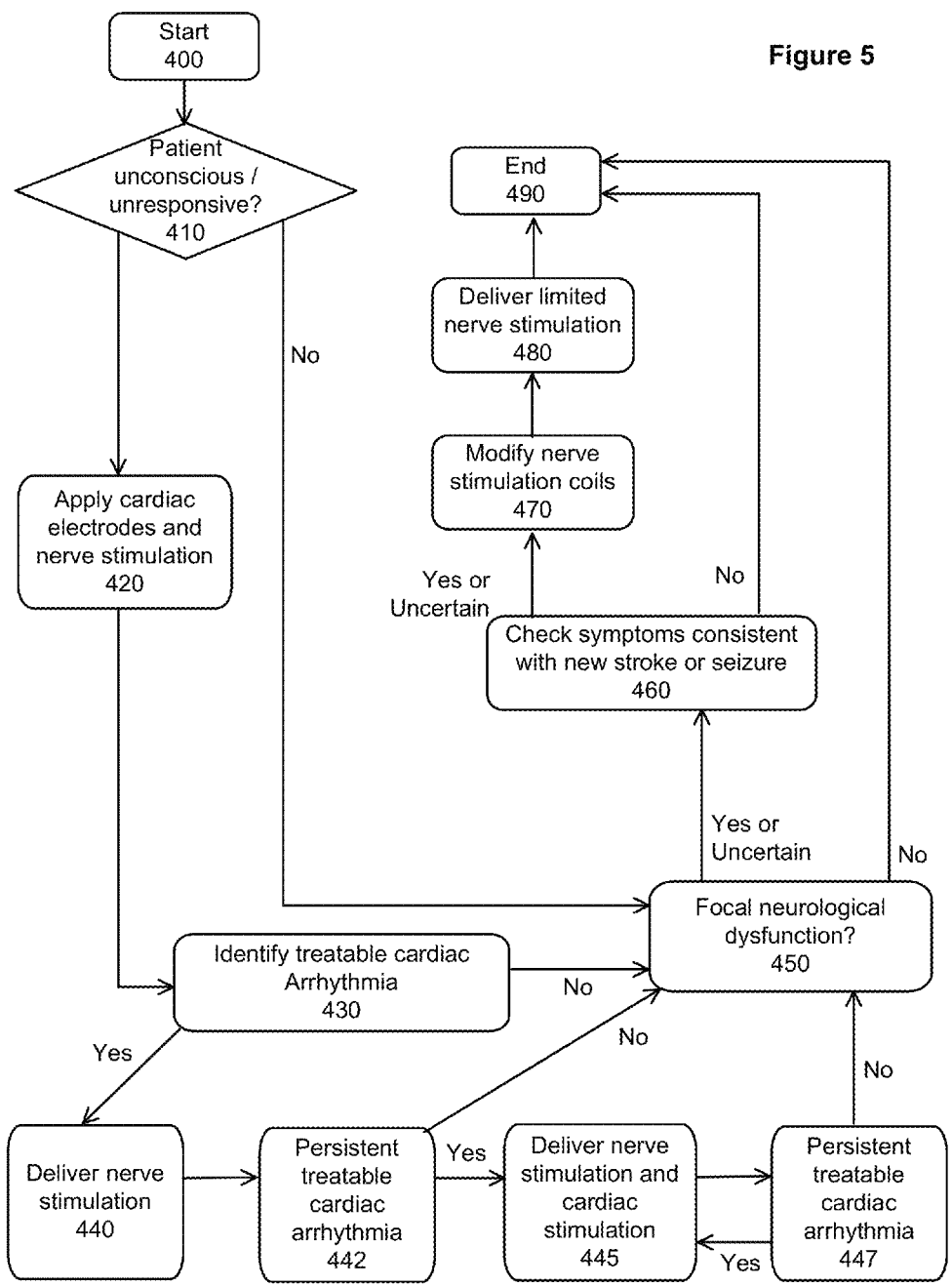
FIG. 5 includes a flowchart for use of a device such as that shown in FIG. 3 in which both nerve and cardiac stimulation are employed to treat a cardiac arrhythmia, and in which a limited nerve stimulation is employed to treat focal neurological dysfunction.

For example, as shown in FIG. 5, starting 400 with a found patient, if the device is informed by a user that a subject is unconscious 410, the user is first instructed to apply cardiac electrodes and nerve stimulation coils 420 as a general means of treating the patient. The cardiac electrodes, having the ability to detect the electrocardiographic potential, allow the system to identify treatable cardiac arrhythmias 430. If treatable cardiac arrhythmia is identified 430, nerve stimulation is administered 440 as an initial attempt to reverse the arrhythmia. If ineffective, i.e., if the cardiac arrhythmia is persistent 442, then nerve stimulation in conjunction with cardiac stimulation is administered 445; this step of combined stimulation may be repeated if the cardiac arrhythmia remains persistent 447. If, after some restricted number of iterations, the cardiac arrhythmia resolves, the patient is then evaluated for focal neurological dysfunction 450, which—if found—is then assessed for the possibility of being caused by stroke of seizure 460. In the case of certainty or even the possibility that focal neurological dysfunction is present or related to stroke or seizure, the nerve stimulation coils are modified 470 in a manner that limits the number and type of nerves they stimulate. In some embodiments, the modification of the stimulation coils 470 involves introducing a member or material that blocks, absorbs, or otherwise modifies the magnetic or electrical field generated near a certain part of the body; in some embodiments, the modification 470 involves altered current flow through the stimulation coil or portion of the stimulation coil; in other embodiments, the modification 470 involves replacing the originally applied stimulation coil 420 with a different stimulation coil. After modification of the stimulation coils 470, limited nerve stimulation is delivered 480 to the subject as a means to treat the residual focal neurological dysfunction that is consistent with stroke or seizure.

The method-of-use of the device exemplified in FIG. 5 also allows for the treatment of focal neurological dysfunction identified 450 in patients who are determined to be conscious 410, otherwise using the steps for limited nerve stimulation 460, 470, 480 described previously.

In some embodiments used in a manner similar to that shown in FIG. 5, modification of the stimulation coils 470 is unnecessary for the treatment of isolated focal neurological dysfunction consistent with stroke or seizure. This can be accomplished if use of the stimulation coils in the original application 420 does not cause harm to the subject who has a normal cardiac rhythm.

What is claimed is:

1. A method for treating a subject exhibiting neurological dysfunction with a stimulation control system comprising a stimulation control device, a cardiac stimulation end device, and a neural stimulation end device, the stimulation control system capable of controlling delivery of stimulation to both the heart and one or more neural structures, the method comprising:

receiving, at the stimulation control device, data regarding a determination of a state of consciousness of the subject;

based on the state of consciousness, receiving, by the stimulation control device, data identifying one or more symptoms or signs exhibited by the subject indicative of a global neurological dysfunction condition or a focal neurological dysfunction condition; and based on the identified symptoms or signs:
  determining, by the stimulation control device, whether to deliver stimulation to the subject by one or both of the cardiac stimulation end device and the neural stimulation end device,
  determining, by the stimulation control device, one or more parameters of stimulation energy to be provided to the applied end device, the determination in accordance with the identified symptoms or signs, and
  delivering, by one or both of the cardiac stimulation end device and neural stimulation end device, one or more types of stimulation energy to the subject based on the one or more parameters.

2. The method of claim 1, wherein receiving data regarding the determination of the state of consciousness of the subject comprises receiving an indication-that the subject is unconscious and wherein the identified one or more symptoms or signs exhibited by the subject are indicative of the global neurological dysfunction condition, the method further comprising identifying a treatable cardiac arrhythmia arising in the heart, wherein the stimulation control device controls a serial or substantially simultaneous delivery of cardiac stimulation via the cardiac stimulation end device and delivery of neural stimulation via the neural stimulation end device.

3. The method of claim 2, further comprising:
  receiving, by the stimulation control device, data indicating restoration of normal cardiac rhythm due to the delivered cardiac stimulation;
  ceasing, by the stimulation control device, delivery of the cardiac stimulation via the cardiac stimulation end device,
  determining, by the stimulation control device, whether the subject exhibits additional symptoms or signs indicative of the focal neurological dysfunction condition, and
  responsive to the determination, controlling, by the stimulation control device, delivery of neural stimulation via the neural device.

4. The method of claim 1, wherein receiving data regarding the determination of the state of consciousness of the subject comprises receiving an indication that the subject is conscious and wherein the identified one or more symptoms or signs exhibited by the subject are indicative of the focal neurological dysfunction condition, the method further comprising identifying a stroke or seizure condition arising in the neural structures in the subject, wherein the stimulation control device controls the delivery of neural stimulation to a cranial or peripheral nerve of the subject with the neural stimulation end device.

5. The method of claim 1, wherein the stimulation control device controls a substantially simultaneous delivery of both cardiac and neural stimulation with both end devices, and wherein the delivery of the neural stimulation is initiated prior to initiation of the delivery of the cardiac stimulation.

6. The method of claim 1, wherein the stimulation control device controls a substantially simultaneous delivery of both cardiac and neural stimulation with both end devices, and wherein the delivery of cardiac stimulation is ceased prior to cessation of the delivery of the neural stimulation.

7. The method of claim 1, wherein the delivery of neural stimulation energy via the neural stimulation end device comprises delivering neural stimulation energy to a neural structure.

8. The method of claim 1, wherein the data identifying one or more symptoms or signs is received by the stimulation control device from one of the cardiac stimulation end device or the neural stimulation end device.

9. The method of claim 1, the method further comprising:
  subsequent to delivering neural stimulation energy with the neural stimulation end device without delivering cardiac stimulation energy with the cardiac stimulation end device, receiving, by the stimulation control device, data indicating persistence of cardiac arrhythmia arising in the heart; and
  responsive to receiving the data, controlling, by the stimulation control device, delivery of both cardiac and neural stimulation energy via the cardiac stimulation end device and neural stimulation end device, respectively.

* * * * *